United States Patent
Hughes et al.

(10) Patent No.: US 10,398,372 B2
(45) Date of Patent: Sep. 3, 2019

(54) PAIN ASSESSMENT METHOD AND SYSTEM

(71) Applicant: ePAT Pty Ltd, Subiaco (AU)

(72) Inventors: Jeff Hughes, Highgate (AU); Kreshnik Hoti, Willetton (AU); Mustafa Abdul Wahed Atee, Ballajura (AU)

(73) Assignee: ePAT Pty Ltd, Subiaco, Western Australia (AU)

( * ) Notice: Subject to any disclaimer, the term of this patent is extended or adjusted under 35 U.S.C. 154(b) by 112 days.

(21) Appl. No.: 15/435,987

(22) Filed: Feb. 17, 2017

(65) Prior Publication Data

US 2017/0156661 A1 Jun. 8, 2017

Related U.S. Application Data (63) Continuation of application No. PCT/AU2015/000501, filed on Aug. 18, 2015.

(30) Foreign Application Priority Data

Aug. 18, 2014 (AU) ............................... 2014903226

(51) Int. Cl.
*A61B 5/00* (2006.01)
*G06F 19/00* (2018.01)
(Continued)

(52) U.S. Cl.
CPC .......... *A61B 5/4824* (2013.01); *A61B 5/0013* (2013.01); *A61B 5/0077* (2013.01);
(Continued)

(58) Field of Classification Search
CPC ... A61B 5/1113; A61B 5/1115; A61B 5/1128; A61B 5/7275; A61B 90/30; A61B 5/411;
(Continued)

(56) References Cited

U.S. PATENT DOCUMENTS 5,653,739 A * 8/1997 Maurer ................... A61N 1/08
604/890.1
6,018,675 A * 1/2000 Apkarian ............. A61B 5/4824
600/407

(Continued)

FOREIGN PATENT DOCUMENTS

EP       2317451 A2    5/2011
JP    2001043345 A    2/2001
(Continued)

OTHER PUBLICATIONS

International Preliminary Report on Patentability dated Aug. 8, 2016 in International Application No. PCT/AU2015/000501. 11 pages.
(Continued)

*Primary Examiner* — Aklilu K Woldemariam
(74) *Attorney, Agent, or Firm* — Kilpatrick Townsend & Stockton LLP (57) ABSTRACT

The present disclosure provides a method for determining an effect of a drug on pain experienced by a patient. The method comprises providing reference information concerning at least one visible and/or audible feature that is indicative of a level of the pain. The method further comprises capturing information indicative of the at least one visible and/or audible feature, respectively, from the patient comprising observing the patient directly or indirectly after administering the drug to the patient. In addition, the method comprises determining pain indicating information associated with a level of pain experienced by the patient using the captured information. The method also comprises comparing the pain indicating information with the provided reference information to determine the effect of the drug on the pain experienced by the patient.

16 Claims, 3 Drawing Sheets

(51) Int. Cl.
*A61B 5/107* (2006.01)
*A61B 5/16* (2006.01)
*G06K 9/00* (2006.01)

(52) U.S. Cl.
CPC ............ *A61B 5/1079* (2013.01); *A61B 5/165* (2013.01); *A61B 5/4803* (2013.01); *A61B 5/4848* (2013.01); *A61B 5/7278* (2013.01); *G06F 19/3456* (2013.01); *A61B 5/0022* (2013.01); *A61B 2503/04* (2013.01); *A61B 2503/08* (2013.01); *A61B 2576/00* (2013.01); *A61B 2576/02* (2013.01); *G06K 9/00221* (2013.01)

(58) Field of Classification Search
CPC ..... A61B 5/002; A61B 8/0808; A61B 5/1112; A61B 5/1455; A61B 5/0013; A61B 5/0022; A61B 5/024; A61B 5/0002; A61B 5/00; A61B 5/082; A61B 8/08; A61B 5/055; A61B 5/4824; A61B 5/16; A61B 5/168; A61B 5/4064; A61B 5/7239; A61B 5/0051; A61B 5/4519; A61B 5/483; A61B 6/037; A61B 6/506; A61B 6/508; A61B 2503/04; A61B 2503/08; A61B 2576/00; A61B 2576/02; A61B 5/0077; A61B 5/1079; A61B 5/165; A61B 5/4803; A61B 5/4848; A61B 5/7278; A61B 5/444; A61G 7/002; A61M 2021/005; A61M 2205/3561; A61M 2210/12; A61M 5/1723; A61M 2005/1405; G06F 19/30; G06F 19/00; G06F 19/321; G06F 19/325; G06F 19/3456; G06K 9/00302; G06K 9/00127; G06K 9/00221; G06K 9/00335; G08B 21/0492; G16H 10/60; G16H 20/10; G16H 10/20; A61K 49/0054; A61K 51/044; A61K 51/0491; B23P 19/00; G06T 7/0012; G01N 33/5008
USPC ............... 382/128, 131, 132, 130; 324/309; 600/407, 409, 410, 300, 481, 528, 553
See application file for complete search history.

(56) References Cited

U.S. PATENT DOCUMENTS

| | | | | |
|---|---|---|---|---|
| 6,640,130 | B1* | 10/2003 | Freeman | A61B 5/0059 382/128 |
| 7,502,498 | B2* | 3/2009 | Wen | G06F 19/3418 382/128 |
| 8,725,669 | B1* | 5/2014 | Fu | A61B 5/0476 706/22 |
| 9,095,266 | B1* | 8/2015 | Fu | A61B 5/0476 |
| 2002/0042563 | A1* | 4/2002 | Becerra | A61B 5/055 600/407 |
| 2002/0173723 | A1* | 11/2002 | Lewis | A61B 5/0059 600/473 |
| 2003/0181516 | A1* | 9/2003 | Krylov | A61K 31/35 514/460 |
| 2004/0204644 | A1* | 10/2004 | Tsougarakis | G01R 33/56 600/410 |
| 2006/0042631 | A1* | 3/2006 | Martin | A61B 5/0836 128/207.18 |
| 2006/0178595 | A1* | 8/2006 | Schatteman | A61B 5/00 600/553 |
| 2007/0273504 | A1* | 11/2007 | Tran | A61B 5/0022 340/539.12 |
| 2008/0004904 | A1* | 1/2008 | Tran | A61B 5/0006 705/2 |
| 2010/0010392 | A1* | 1/2010 | Skelton | A61B 5/1116 600/595 |
| 2010/0072996 | A1* | 3/2010 | Jacobson | A61N 2/002 324/309 |
| 2013/0041258 | A1* | 2/2013 | Patrick | A61B 8/00 600/439 |
| 2013/0127620 | A1 | 5/2013 | Siebers et al. | |
| 2014/0344740 | A1* | 11/2014 | Kaula | A61N 1/37247 715/771 |
| 2015/0324544 | A1* | 11/2015 | Maslowski | G16H 10/20 600/409 |
| 2016/0287166 | A1* | 10/2016 | Tran | H04B 1/3827 |
| 2017/0164876 | A1* | 6/2017 | Hyde | G16H 50/30 |

FOREIGN PATENT DOCUMENTS

| | | |
|---|---|---|
| JP | 2003091591 A | 3/2003 |
| JP | 2006158490 A | 6/2006 |
| WO | 2013055528 A1 | 4/2013 |

OTHER PUBLICATIONS

Supplemental European Search Report, European Patent Application No. 15833312, dated Mar. 8, 2018, 11 pages.

Ashraf, et al., "The Painful Face—Pain Expression Recognition Using Active Appearance Models," Nov. 12, 2007, ICMI '07: Proceedings of the 9th International Conference on Multimodal Interfaces, pp. 9-14.

Mansor, et al., "Automatically Infant Pain Recognition Based on LDA Classifier," 2012, International Symposium on Instrumentation & Measurement, Sensor Network and Automation (IMSNA), pp. 380-382.

Sotocinal, et al., "The Rat Grimace Scale: A partially automated method for quantifying pain in the laboratory rat via facial expressions," Jul. 29, 2011, Molecular Pain, vol. 7, No. 1, p. 55, 10 pages.

* cited by examiner

FIG. 3

PAIN ASSESSMENT METHOD AND SYSTEM

CROSS-REFERENCES TO RELATED APPLICATIONS

This application is a continuation application of PCT application PCT/AU2015/000501 entitled "A PAIN ASSESSMENT METHOD AND SYSTEM," filed on Aug. 18, 2015, which claims priority to Australian Patent Application No. 2014903226, filed on Aug. 18, 2014, which are herein incorporated by reference in their entirety for all purposes.

FIELD OF THE INVENTION

The present invention relates to a pain assessment system and a method for determining an effect of a drug on pain of a patient.

BACKGROUND OF THE INVENTION

Pain assessment amongst non-communicative patients such as patients with dementia or infants is difficult and highly subjective. Patients with dementia commonly have pain, and this pain often goes undetected and under treated. Undiagnosed pain can manifest in other symptoms such as increased confusion and behavioural change such as agitation and aggression which may lead to difficulties with delivering care, increased medication use and carer burden.

Existing tools that are based on American Geriatric Society's (AGS) guidelines are not automated, highly subjective resulting in significant variability, and hence inconsistencies in pain management of patients.

There is need for improvement.

BRIEF SUMMARY OF THE INVENTION

In accordance with a first aspect of the present invention, there is provided a method for determining an effect of a drug on pain experienced by a patient, the method comprising:
  providing reference information concerning at least one visible and/or audible feature that is indicative of a level of the pain;
  capturing information indicative of the at least one visible and/or audible feature, respectively, from the patient comprising observing the patient directly or indirectly after administering the drug to the patient;
  determining pain indicating information associated with a level of pain experienced by the patient using the captured information; and
  comparing the pain indicating information with the provided reference information to determine the effect of the drug on the pain experienced by the patient.

In an embodiment, the step of using the captured information to determine the pain indicating information is conducted automatically using an algorithm.

In an embodiment, the step of providing the reference information comprises capturing further information indicative of the at least one visible and/or audible feature of the patient before the drug is expected to have an effect on the pain experienced by the patient. In this embodiment, the method may further comprise a step of using the captured further information to determine the reference information indicative of the reference level of pain. This step may be conducted automatically using the algorithm. It will be appreciated that the further information may be captured before administration of the drug. However, it is envisaged that the step of capturing the further information may alternatively be conducted after administration of the drug and before the drug is expected to have an effect on the pain experienced by the patient.

In an alternative embodiment, the reference information is indicative of an expected level of pain after administration of the drug. For example, the reference information may relate to statistical information in relation to the drug that is administered to the patient.

In some embodiments, the drug relates to an analgesic for primarily reducing pain. However, any other suitable drug is envisaged that is expected to reduce or increase the pain experienced by a patient. For example, the drug may have a secondary effect such as a side effect in that pain experienced by the patient is reduced or increased.

The method may comprise a step of receiving and storing information in relation to the drug. The information may include one or more of the following:
  name of the drug;
  manufacturer of the drug;
  dose of the drug that is administered;
  content of the drug;
  pharmaceutical formulation;
  route of administration of the drug, such as oral, topical, transdermal or injectable;
  an estimated time period for the drug to have an expected effect on the patient; and
  form of the drug, such as a tablet, capsule or liquid.

In an embodiment, the method comprises a step of receiving and storing information in relation to the patient. The information may include one or more of the following:
  name of the patient;
  age of the patient;
  weight of the patient;
  height of the patient;
  sex of the patient;
  data in relation to the effect of the or a further drug on the patient such as a time period for the drug to effect a reduction of pain;
  allergies;
  side effects; and
  data in relation to previous drug administration.

In an embodiment, the method comprises a step of using the information in relation to the drug and/or the information in relation to the patient to estimate a time period for the drug to have an expected effect on pain experienced by the patient such as a pain reducing effect. In this embodiment, the step of capturing the information indicative of the visible and/or audible feature of the patient may be conducted after the estimated time period has expired.

The method may further comprise a step of communicating the estimated time period to a user and/or the patient such that the information indicative of the at least one visible and/or audible feature can be captured after the estimated time period has expired. The step of communicating the estimated time period may be conducted by virtue of at least one of visual, audio and tactile feedback.

In a specific embodiment, the method comprises a step of identifying a cause of the pain experienced by the patient based on the determined effect of the drug on pain. Additionally or alternatively, the method may comprise a step of determining treatment of the pain experienced by the patient based on the determined effect of the drug on pain. For example, if it is determined that a pain reducing effect of the drug is below a predetermined threshold, an alternative drug may be identified for administering to the patient or a further time period may be estimated for administration of the drug.

The at least one visible and/or audible feature of the patient may comprise a facial feature of the patient. For example, the step of capturing the information may comprise capturing an image of at least one facial feature of the patient. It should be appreciated that a still image or a moving image may be captured.

The step of determining the pain indicating information may be conducted automatically using the captured image. In this example, the step comprises using an algorithm to determine the pain indicating information. For example, a facial feature may be identified and compared with predetermined data such that the pain indicating information can be determined. The predetermined data may be indicative of facial pain indicators, such as according to American Geriatric Society's (AGS) widely accepted pain indicators. For example, the mouth of the patient may be identified and positional information of the mouth may be determined, such as a size of the mouth, a position of the lips or a position of the corner lip. In this example, a widely accepted pain indicator is for example pulling at corner lip. Thus, by comparing the positional information of the mouth to the predetermined data indicative of the pain indicators, it can be determined whether the patient pulls at the corner lip, i.e. experiences pain.

Additionally or alternatively, the at least one visible and/or audible feature of the patient may relate to a vocal feature. For example, the step of capturing the information may comprise capturing a frequency spectrum from the voice of the patient.

The step of determining the pain indicating information may be conducted automatically using the captured frequency spectrum. For example, a frequency spectrum from the voice of the patient may be identified and compared with predetermined data such that the pain indicating information can be determined.

In accordance with a second aspect of the present invention, there is provided a pain assessment system comprising:
  an interface for receiving information indicative of at least one visible and/or audible feature of a patient, the at least one visible and/or audible feature being capable of indicating pain;
  a processor arranged to use the received information to determine pain indicating information indicative of a level of pain experienced by the patient after administering a drug;
  wherein the system is arranged such that an effect of the drug on pain experienced by the patient can be determined by comparing the pain indicating information with reference information indicative of a reference level of pain.

In some embodiments, the drug relates to an analgesic for primarily reducing pain. However, any other suitable drug is envisaged that is expected to reduce or increase pain experienced by a patient. For example, the drug may have a secondary effect in that pain experienced by the patient is reduced or increased.

In an embodiment, the processor is arranged to automatically determine the pain indicating information using an algorithm.

In an embodiment, the reference information is indicative of a level of pain experienced by the patient before the drug is expected to have an effect on the pain experienced by the patient. In this regard, the reference information may be determined by the processor by using further information indicative of the at least one visible and/or audible feature of the patient captured before the drug is expected to have an effect on the pain experienced by the patient. The processor may be arranged to automatically determine the reference information using the algorithm.

In an alternative embodiment, the reference information is indicative of an expected level of pain after administration of the drug. For example, the reference information may relate to statistical information in relation to the drug that is administered to the patient.

The system in accordance with embodiments of the present invention has significant advantages. In particular, the pain experienced by a specific patient can be objectively assessed thereby determining an objective measurement of an effectiveness of a drug on the pain experienced by the patient. Further, pain can be assessed for patients that are incapable of communicating the experienced pain, such as dementia patients or infants. Also, administration of a drug can be customized for a specific patient which may result in a more tailored pain management for the patient.

In an embodiment, the interface of the system may further be arranged to receive information in relation to the drug. The information may include one or more of the following:
  name of the drug;
  manufacturer of the drug;
  dose of the drug that is administered;
  content of the drug;
  pharmaceutical formulation;
  route of administration of the drug, such as oral, topical, transdermal or injectable;
  an estimated time period for the drug to have an expected effect on the patient; and
  form of the drug, such as tablet, capsule, gel, patch or liquid.

Additionally or alternatively, the interface of the system may be arranged to receive information in relation to the patient. The information may include one or more of the following:
  name of the patient;
  age of the patient;
  weight of the patient;
  height of the patient;
  sex of the patient;
  data in relation to the effect of the or a further drug on the patient such as a time period for the drug to effect a reduction of pain;
  allergies;
  side effects; and
  data in relation to previous drug administration.

In at least one embodiment, the processor is arranged to use the information in relation to the drug and/or the information in relation to the patient to estimate a time period for the drug to have an expected effect on pain experienced by the patient, such as a pain reducing effect. Additionally or alternatively, the time period may be estimated using predetermined data such as population based pharmacokinetics. For example, the estimated time period may be associated with a maximum effect of the drug. In this way, the pain indicating information can be determined for a level of pain experienced by the patient after the estimated time period has expired.

The system may further be arranged to communicate the estimated time period to the patient, for example by virtue of at least one of the following: visual, audio and tactile feedback.

In a specific embodiment, the interface of the system is arranged to transmit information indicative of the estimated time period and/or the determined effect of the drug on pain via a communications network. The communications network may for example be the Internet or a peer to peer network such as Bluetooth.

In a specific embodiment, the processor of the system is arranged to determine treatment for the patient based on the determined effect of the drug on pain. For example, if the system determines that a pain reducing effect of the drug on the pain experienced by the patient is below a predetermined threshold, the processor may identify an alternative drug for reducing pain and/or determine a further time period for further administration of the or another drug.

The at least one visible and/or audible feature of the patient may comprise a facial feature of the patient. For example, the received information indicative of the at least one feature may comprise an image of the facial feature. It should be appreciated that the image may be a still image or a moving image. For example, the image may be captured by a capturing element such as a camera of a user computing device that may be located remotely relative to the system.

Additionally or alternatively, the at least one visible and/or audible feature may comprise a vocal feature. For example, the received information indicative of the at least one feature may comprise a frequency spectrum from the voice of the patient. The frequency spectrum may be captured by a capturing element such as a recorder or a microphone of a user computing device that may be located remotely relative to the system.

An additional or alternative visible or audible feature of the patient may include one or more of the following:
- behavioural change,
- psychological change,
- physiological change, and
- physical change.

It should be appreciated that the system may be arranged to receive and store information indicative of any suitable visible and/or audible feature of the patient that is capable of indicating pain.

In accordance with a third aspect of the present invention, there is provided a software application installable on a user computing device, the application when installed on the user computing device causing the user computing device to operate in accordance with a pain assessment system arranged to:
- after administering a drug to a patient, receive information indicative of at least one visible and/or audible feature of a patient from a capturing element of the user computing device, the at least one visible and/or audible feature being capable of indicating pain;
- transmit the received information to a pain assessment system via a communications network such that the pain assessment system can determine an effect of the drug on pain experienced by the patient by determining pain indicating information indicative of a level of pain experienced by the patient after administration of the drug using the received information and by comparing the pain indicating information with reference information indicative of a reference level of pain; and
- receive information indicative of the determined effect of the drug on pain experienced by the patient from the pain assessment system via the communications network.

In accordance with a fourth aspect of the present invention, there is provided a pain assessment system comprising:
- a capturing element for capturing information indicative of at least one visible and/or audible feature of a patient, the at least one visible and/or audible feature being capable of indicating pain;
- a processor arranged to use the captured information to determine pain indicating information indicative of a level of pain experienced by the patient after administration of a drug to the patient;
- wherein the system is arranged such that an effect of the drug on pain experienced by the patient can be determined by comparing the pain indicating information with reference information indicative of a reference level of pain.

The invention will be more fully understood from the following description of specific embodiments of the invention. The description is provided with reference to the accompanying drawings.

DETAILED DESCRIPTION OF THE INVENTION

Embodiments of the invention relate to a method and a system for determining an effect of a drug on pain experienced by a patient after administration of the drug to the patient. In this regard, information indicative of at least one visible and/or audible feature of a patient is captured that is capable of indicating pain experienced by the patient. The feature may for example be a facial feature or a vocal feature of the patient. Accordingly, the information may be in the form of an image of the face of the patient or a frequency spectrum from the voice of the patient.

Using the captured information, quantitative pain indicating information is determined indicative of a level of pain experienced by the patient after a time period when the drug is expected to have an expected effect on pain. By comparing the determined pain indicating information with reference information indicative of a reference level of pain, a patient-specific effect of the drug on pain can be determined. In this way, the level of pain experienced by a patient can be objectively assessed which is particularly advantageous for patients that are incapable of communicating the severity of pain that they experience, such as dementia patients or infants. Further, a responsiveness of the patient to administration of the drug can be determined.

Furthermore, the method and system in accordance with embodiments of the present invention have a real time functionality and capability which is particularly advantageous for its applicability for point-of-care use.

Suitable exemplary applications of the method and the system for determining an effect of a drug on pain experienced by a patient may be used in the field of, but not limited to, dementia, autism and paediatrics. For example, the pain assessment system in accordance with embodiments may be used for dementia patients, autistic patients or infants and/or other population groups with difficulties in communicating pain. However, it will be appreciated that embodiments of the invention may be used in any suitable field in which a patient receives a drug. For example, the pain assessment system in accordance with an embodiment of the invention may be used for research purposed to determine the effect of a drug on a particular group of patients, for example infants experience post-operative pain or pain associated with immunisation.

In one example, the reference information is indicative of an expected level of pain after administration of the drug. The reference information may be derived from statistical information in relation to the drug. For example, the pain indicating information and the reference information may be in the form of a pain score. The pain score may for example be within a range from 1 to 10. In this way, it can be determined whether the level of pain experienced by the patient after administration of the drug is within an acceptable range of the expected level of pain. For example, the level of pain experienced by the patient after administration of the drug may be determined to be 5 whereas no pain is associated with a pain score of 0 and maximum pain with 10. The expected level of pain after administration of the drug may be associated with a pain level of 3. By comparing the level of pain experienced by the patient with the expected level of pain after administration of the drug, it can be determined whether the effect of the drug on pain is acceptable or whether further administration of the drug or an alternative drug is necessary.

Figure 1:
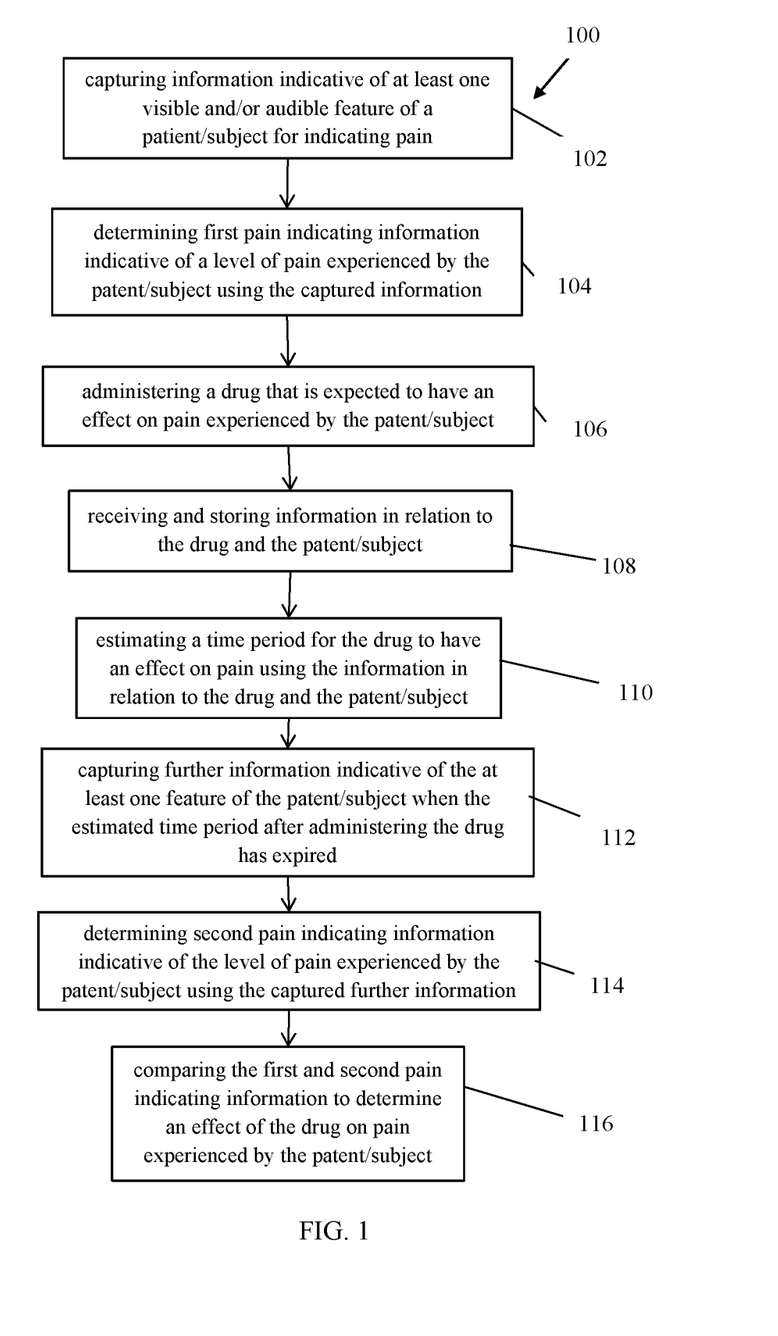
FIG. 1 is a flow chart of a method in accordance with an embodiment of the present invention.

Referring now to FIG. 1, there is shown a flow chart of a method for determining an effect of a drug on pain experienced by a patient in accordance with an embodiment. In a first step 102, first information is captured indicative of at least one visible and/or audible feature of a patient that is capable of indicating pain experienced by the patient. This step 102 is conducted before the drug has an expected effect on the pain experience by the patient. For example, the step 102 may be conducted before the drug is administered or after the drug has been administered, but before the drug is expected to have an effect on the pain experienced by the patient.

The at least one feature may comprise a facial feature, a vocal feature or any other suitable feature or combination of features that is capable of indicating pain of the patient.

Exemplary further features may include behaviour of the patient, psychological change, physiological change and physical change. Together with the facial features and vocal features, these exemplary pain indicators relate to American Geriatric Society's (AGS) widely accepted pain indicators. For example, AGS's facial pain indicators may include lowering of the brow, raising of the cheek, tightening of eyelids, wrinkling of the nose, raising of upper lip, pulling at corner lip, horizontal mouth stretch, parting lips and closing eyes. Further, AGS's vocal pain indicators may include noisy pain sounds, repetitive vocal requests, groaning, moaning, crying, screaming, howling and sighing.

Pain indicators shown in the movement of a patient may include altered or random leg/arm movement, frequent changing of body positions, freezing, guarding/touching a body part, moving away when approached, altered sitting/standing/walking and pacing/wandering. Pain indicators shown in the behaviour of a patient may include introvert or altered behaviour, verbally offensive/cursing, aggressiveness, phobia of touch, inappropriate behaviour, confusion and distress. Pain indicators shown in the activity of a patient may include resisting care such as food or medicine, prolonged resting, altered sleep cycle and altered routines. Pain indicators shown in the body of a patient may include profuse sweating, pale or flushed colour, fever, rapid breathing, injuries and medical conditions such as arthritis or shingles.

In the specific example shown in FIG. 1, the at least one feature comprises a plurality of facial features of the patient that is captured by a capturing device such as a camera. Consequently, the first information indicative of the facial features may be in the form of an image, such as a still image or a moving image.

In a further step 104, the captured first information from step 102 is used to determine reference information that is indicative of a reference level of pain of the patient using the captured information from step 102. In this example, the reference level of pain is the level of pain experienced by the patient before the drug is administered.

This step 104 may be conducted automatically using an algorithm. With reference to the specific example of facial features, the algorithm may be arranged to identify a plurality of facial features from the image of the patient captured by the camera. Further, the algorithm compares the identified facial features with predetermined data such that the reference information can be determined.

Suitable exemplary facial features may include the brow, the cheek, the eyes, the nose, and the lip. For example, using the image of the face of the patient, the brow of the patient is identified. Further, positional information of the brow relative to the face of the patient is determined and compared to predetermined data that is indicative of widely accepted pain indicators such as AGS's pain indicators. Referring to the example of the brow, by determining positional information of the brow of the patient relative to the face, it may be determined that the patient lowers the brow which is one of the widely accepted pain indicators. Thus, it may be concluded that the patient experiences pain. In this regard, the positional information of the brow may be compared to positional information of the brow of patients who experience no pain such that it can be determined whether the patient lowers the brow. When it is determined, that the patient's facial feature such as the brow conforms to a pain indicator, a predefined score of pain may be allocated to this facial feature.

A further facial feature may relate to the eyes of the patient. For this facial feature, a pain indicator may for example be tightening the eyelids or closing the eye. By determining positional information of the eye and the eye lids, it can be determined whether this facial feature conforms to one of AGS's pain indicators and a predefined score of pain may be allocated.

For the facial feature of the mouth, a number of AGS's pain indicators relate to raising the upper lip, pulling at corner lip, horizontal mouth stretch and parting lips. In this regard, positional information of the mouth of the patient may be determined, such as a size, a position of the mouth relative to the face, a position of the lips relative to each other or a position of corners of the mouth. In this way, it can be determined whether the mouth of the patient conforms to any one or more of the above mentioned pain indicators.

A predefined score of pain may be allocated to each of the identified pain indicators. For example, a binary scoring system may be used in which presence of pain allocates a score of 1 whereas absence of pain is allocated a score of 0. Once scores of pain have been allocated to the identified facial features, a total level of pain for the plurality of facial features may be determined.

In a specific example, a software program may be used for identifying the plurality of facial features. For example, the software program may explore a method of identifying key muscles of the face of a patient and then linking points of the identified key muscles to create a map of the face of a patient. In this way, facial expressions may be analysed using the FACS (Facial Action Coding System) methodology. FACS is an anatomically based system and describes facial codings through specific muscle movement. Specifically, FACS divides facial muscles into action groups that typically comprise a plurality of muscles. The plurality of muscles within an action group is associated with predefined actions such as raising the inner left eyebrow or raising the left outer lip. Activation of a number of action groups may be indicative of a facial expression, such as the expression of happiness or pain.

The exemplary software program may further be arranged to link the aforementioned measurements of the identified facial key muscles with human expressions such as presence or absence of pain. In this regard, the exemplary software program may use a database of images with facial expression in natural environments to learn from real examples.

In a specific example in which a level of pain experienced by infants is assessed, step 104 of the method 100 may use the physical features (facial expressions, legs movements, activity), together with vocalisation (cry nature and intensity), and behavioural features (level of consolability) for determining information indicative of a level of pain experienced by the infant.

The next step 106 relates to administering the drug to the patient for which the effect on pain experienced by the patient is determined. The drug may be an analgesic with the primary function of reducing pain experienced by the patient. However, any other suitable drug is envisaged that may reduce or increase the pain experienced by the patient. For example, the drug may have a secondary effect such as a side effect that reduces or increases the pain experienced by the patient.

In a further step 108, information is received and stored in relation to the patient and the drug that is administered to the patient in step 106. For example, the information in relation to the drug may include one or more of the following: name of the drug, manufacturer of the drug, volume or weight of the drug that is administered, content of the drug, state of the drug, such as tablet, capsule, gel, patch or liquid, and an estimated time period for the drug to have an effect on the patient.

The information in relation to the patient may include one or more of the following: name of the patient, age of the patient, weight of the patient, height of the patient, sex of the patient, historical data in relation to the effect of the or a further drug on the patient such as a time period for the drug to have an effect on the patient, allergies, side effects and data in relation to previous drug administration.

In step 110 of the method 100, the information in relation to the patient and the drug from step 108 is used to estimate a time period the drug to have an expected effect on the pain experienced by the patient. The time period for the drug to have an effect on the pain experienced by the patient is dependent on a number of factors. For example, the time period may depend on the dose of the drug that is administered and on whether the drug is administered by injection or orally. Further, the time period may depend on patient specific factors such as the age and weight of the patient.

When the estimated time period has expired after the drug is administered to the patient, second information indicative of the at least one visible and/or audible feature of the patient is captured in step 112. For example, a second image of the facial features of the patient may be taken by the camera.

In a further step 114, pain indicating information is determined indicative of the level of pain experienced by the patient after administration of the drug using the captured second information, such as the second image taken by the camera. In this way, the level of pain can be determined after the drug has been administered to the patient, i.e. when the drug is expected to have an effect on pain of the patient.

In order to determine a patient-specific effect of the drug on pain experienced by the patient, the pain indicating information is compared with the reference information from step 104. In this way, it can be determined whether the responsiveness of the patient to the administered drug is acceptable. For example, if it is determined that the effect of the drug on the pain experienced by the patient is below a predetermined threshold, a cause of the pain may be identified and/or treatment of the patient may be determined. For example, an alternative drug or a further time period for administering the drug may be determined. For this step, the information in relation to the patient and/or the information in relation to the drug may be used.

The treatment may relate to pain management. For example, if it is determined that the effect of the drug on pain is below or exceeds a predetermined pain threshold, further pain management may be necessary. If the drug comprises an analgesic and the determined effect of the drug is below a predetermined threshold, an alternative analgesic may be identified and a time period may be determined for administrating the alternative analgesic. In a further example, if the drug relates to a drug in which a side effect is an increase in pain experienced by the patient and the effect of the drug on pain exceeds a predetermined pain threshold, an analgesic may be identified for administering to the patient.

Figure 2:
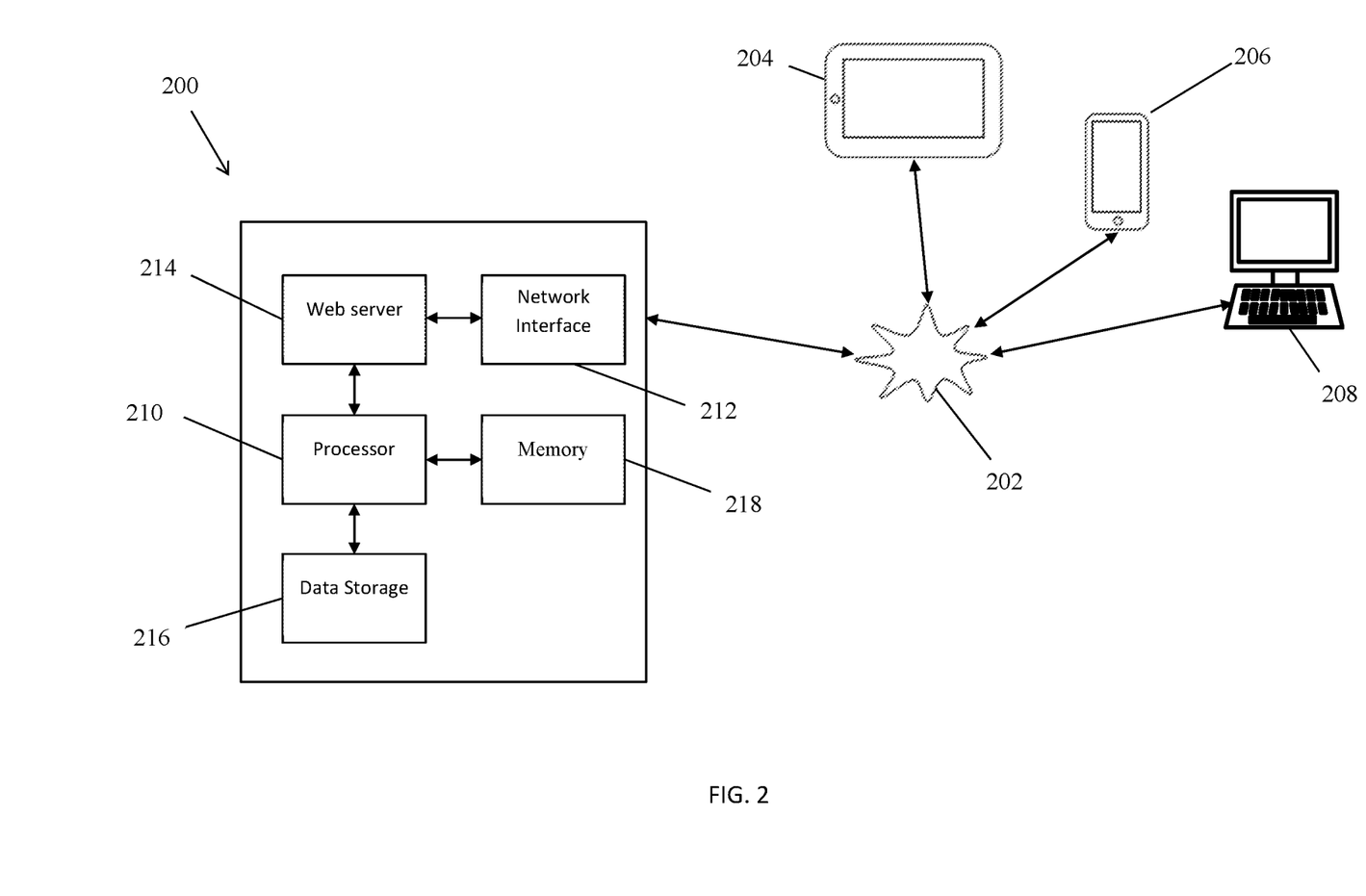
FIG. 2 is a schematic representation of a pain assessment system in accordance with an embodiment of the present invention.

Referring now to FIG. 2, there is shown a schematic representation of a pain assessment system 200 for determining an effect of a drug on pain experienced by a patient. In this example, the pain assessment system 200 is in the form of a computer server that is accessible through a communications network 202 from user computing devices 204, 206, 208. The communications network 202 may be any suitable network such as the Internet, cloud computing or a peer-to-peer network such as Bluetooth. In this example, the user computing devices 204, 206, 208 include a tablet computer 204, a smartphone 206, and a personal computer 208. However, it will be understood that any communications enabled computing device that is capable of communicating with the pain assessment system 200 is envisaged, such as a laptop computer or PDA.

In the present example, the pain assessment system 200 is implemented as a computer server including a processor 210 arranged to control and coordinate operations in the system 200. The system 200 further comprises a network interface 212 which in this example is arranged to facilitate wireless communications with the system 200 through the Internet 202. In the present embodiment as shown in FIG. 2, the system 200 is accessible by the user computing devices 204, 206, 208 through web pages served to the user computing devices 204, 206, 208 by a web server 214. In a specific example, this is realised by software implemented by the processor 210, and through an application programming interface (API) that communicates with the user computing devices 204, 206, 208 using a dedicated application installed on the user computing devices 204, 206, 208. However, other implementations are envisaged.

The system 200 also includes a data storage 216 arranged to store programs, data and information used by the system 200. The system 200 also includes a memory 218 used by the processor 210 to temporarily store data and programs used by the processor 210 to implement functionality in the system 200.

Figure 3:
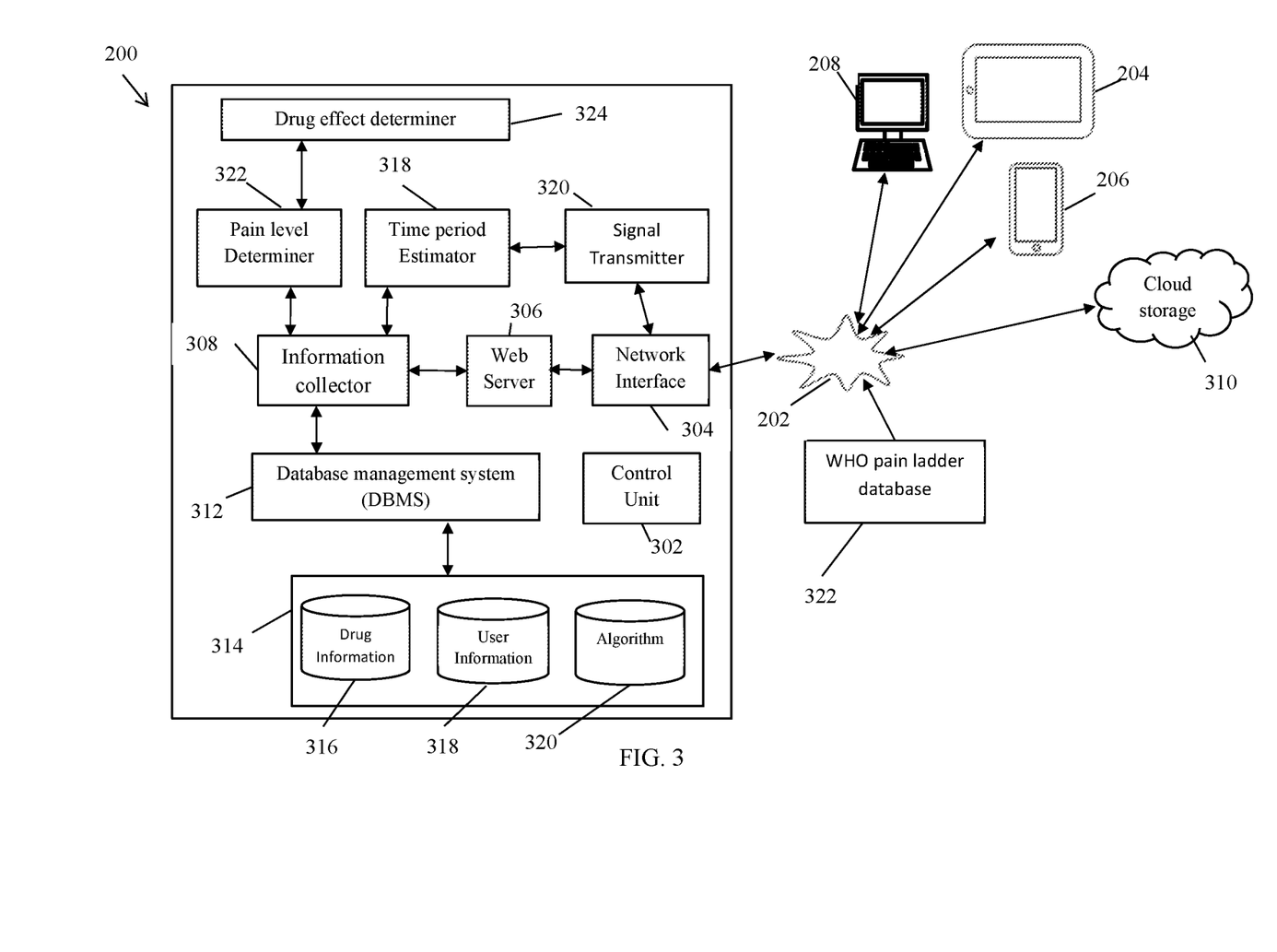
FIG. 3 is an alternative representation of the system of FIG. 2.

A representation of an example implementation of the pain assessment system 200 is shown in FIG. 3, with functional components of the system 200 shown instead of hardware components. It will be understood that the functional components in this example may be implemented using the hardware components shown in FIG. 2 such that network interfaces are provided for facilitating communications with remote user computing devices 204, 206, 208 and implementing actions in response to the communications.

The pain assessment system 200 in this example comprises a control unit 302 for controlling and coordinating operations of the components of the system 200. This control unit 302 may for example be implemented by the processor 210 shown in FIG. 2.

Further, the system 200 has a network interface 304 for facilitating communications through the communications network 202, such as the Internet between the system 200 and remote computing devices, such as user computing devices 204, 206, 208. In this example, a web server 306 of the system 200 is arranged to serve one or more webpages to the user computing device 204, 206, 208 that can be accessed through a browser installed on the user computing device 204, 206, 208 thereby facilitating communications with the system 200.

In this specific example as shown in FIG. 3, the system 200 is arranged to receive at an information collector 308 information indicative of at least one visible and/or audible feature of the patient that is capable of indicating pain experienced by the patient. In this example, the feature comprises at least one facial feature of the patient and the information is in the form of an image taken by a capturing element of the user computing device 204, 206, 208 such as a camera. The captured image may then be transmitted to the system 200 by uploading the captured image using a web page displayed on the user computing device 204, 206, 208 served by the web server 306 of the system 200. Alternatively, the information indicative of the at least one visible and/or audible feature of a patient may be received at the information collector 308 of the system 200 by importing data from a remote database such as a cloud storage 310.

The system 200 is further arranged to receive information at the information collector 308 in relation to the patient and the drug that is administered to the patient. In this regard, part of the information such as information in relation to the patient may be entered into the web page displayed on the user computing device 204, 206, 208 served by the web server 306 of the system 200. A further part of the information such as information in relation to the drug may be imported from a remote database such as from a pharmacokinetics database.

The pain assessment system 200 further comprises a database management system ("DBMS") 312 that is arranged to store the information that is received at the information collector 308 in a data storage 314 of the system 200. A person skilled in the art will appreciate that the information may alternatively be stored in a data storage system that is not part of the system 200. For example, the information may be stored in a cloud storage 310 and may be received at the system 200 through the Internet 202 via the network interface 304.

In this example, the DBMS 312 is arranged to store information in relation to the drug in a drug information database 316 of the data storage 314. The drug that is administered to the patient may relate to an analgesic that has the primary effect of reducing pain of the patient. However, it should be appreciated that any suitable drug is envisaged that has an effect on the pain experienced by the patient, such as pain reducing or increasing effect. For example, a drug may have a secondary effect such as a side effect on the patient in that pain of the patient is reduced or increased.

The information in relation to the drug may include one or more of the following:
name of the drug;
manufacturer of the drug;
dose of the drug that is administered;
content of the drug;
pharmaceutical formulation;
route of administration of the drug, such as oral, topical, transdermal or injectable;
an estimated time period for the drug to have an effect on the patient; and form of the drug, such as tablet, capsule, gel, patch or liquid.

The DBMS 312 is further arranged to store the information in relation to the patient in a patient information database 318 of the data storage 314.

The information in relation to the patient may comprise one or more of the following information:
name of the patient;
age of the patient;
weight of the patient;
height of the patient;
sex of the patient;
data in relation to the effect of the or a further drug on the patient such as a time period for the drug to effect a reduction of pain;
allergies;
side effects; and
data in relation to previous drug administration.

In response to receiving a first image of the facial feature of the patient at the information collector 308, a pain level determiner 322 of the pain assessment system 200 uses the first image to determine information indicative of a first level of pain experienced by the patient. In this particular example, the information represents reference information for a level of pain experienced by the patient before a drug is administered.

The pain level determiner 322 determines the reference information indicative of the reference level of pain experienced by the patient automatically using an algorithm. The algorithm is stored by the DBMS 312 in an algorithm database 316 of the data storage 310. In this particular example, the algorithm that is used for determining the information indicative of a level of pain may identify a facial feature from the first image and compare this identified facial feature with predetermined data such as AMS's widely accepted pain indicators. In this example, the predetermined data is also stored in the algorithm database 316. However, it will be envisaged that the predetermined data may be stored remote relative to the system 200, for example in the cloud storage 310.

The system 200 further comprises a drug effect determiner 324 that may be implemented by the processor 210 shown in FIG. 2. The drug effect determiner 324 determines an effect of the drug on pain experienced by the patient by comparing pain indicating information indicative of the level of pain experienced by the patient after administration of the drug with the reference information from the pain lever determiner 322.

Specifically, when the drug is expected to have an effect on the pain experienced by the patient after the drug is administered to the patient, a second image of the patient's facial feature is captured and received at the information collector 308 of the pain assessment system 200. Depending on a number of factors, the second level of pain may be determined when the drug is expected to have a maximum effect on the pain experienced by the patient such as in a range of 5 to 30 minutes after administering the drug.

Using this second image, the information indicative of the level of pain experienced by the patient is automatically determined at the pain level determiner 322 using the algorithm that is stored in the algorithm database 320. In this way, it can be objectively assessed whether the drug had an effect on pain experienced by the patient. This is particularly advantageous for patients that are incapable of communicating the level of pain such as dementia patients and infants that may not be able to express the intensity of pain to a third person. A further advantage relates to the possibility of applying a more tailored pain management to the patient based on the determined patient-specific effect of the drug on pain.

The system 200 further comprises a time period estimator 326 for estimating a time period for the drug to have an expected effect on pain experienced by the patient after the drug is administered, such as a pain reducing or in some cases a pain increasing effect. In order to estimate the time period, the time period estimator 326 uses information from the information collector 308, such as information in relation to the patient stored in the patient information database 318, information in relation to the drug stored in the drug information database 316 or information such as population based pharmacokinetics that is stored remote relative to the system 200 such as in a cloud storage 310. The estimated time period may be associated with an expected maximum effect of the drug on pain experienced by the patient.

For example, the time period for the drug to have an effect on pain experienced by a patient is dependent on a number of factors such as the method of administering the drug (injection or orally) and the dose of the drug that is administered. The time period estimator 326 may further consider patient-specific factors for estimating the time period such as the age and weight of the patient, previous data in relation to the effect of the drug on pain, and possible side effects. Ranges of typical time periods may include 5 to 30 minutes, 10 to 25 minutes, 10 to 20 minutes and 10 to 15 minutes.

The system 200 is further arranged to make information indicative of the estimated time period accessible to a user computing device 204, 206, 206. This may for example be in the form of an alarm signal. In this regard, the estimated time period is provided to the user computing device 204, 206, 208 by the web server 203 through one or more web pages associated with the system 200. This may be done by using dedicated application software that is installed on the user computing device 204, 206, 208 or in any other suitable manner. For example, the information indicative of the estimated time period may be transmitted to the user computing device 204, 206, 208 causing the user computing device 204, 206, 208 to provide visual, audio or tactile feedback when the estimated time period has expired after the drug is administered. In this way, a second image can be taken by the camera of the user computing device 204, 206, 208 such that the pain level determiner 322 of the system 200 can determine the pain indicating information indicative of the level of pain the patient is experiencing.

The processor 210 of the system 200 may optionally be arranged to determine treatment of the patient based on the determined patient-specific effect of the drug on pain using predetermined information such as information from the WHO pain ladder database 322. For example, if the determined effect of the drug on pain exceeds or is below a predetermined threshold, it may be necessary to administer an additional dose of the drug or an alternative drug to the patient. If an analgesic was administered to the patient and the determined effect of the analgesic on pain of the patient is below a predetermined threshold, an alternative analgesic may be identified and a time period may be determined for administering the alternative analgesic. The information indicative of the alternative analgesic and the time period may be communicated to the user computing device 206, 208, 210 by via the Internet by displaying the information on a webpage served by the web server 306.

In a further specific example, instead of capturing an image of a facial feature of the patient, the at least one visible and/or audible feature of the patient may comprise a vocal feature. For example, a capturing element of the user computing device 206, 208, 210 such as a microphone or a recording device is arranged to record a frequency spectrum from the voice of the patient. Information indicative of the frequency spectrum from the voice of the patient that may for example be in the form of an audio file such as mp3 or way may be transmitted to the system 200 by uploading the audio file using a web page served by the web server 306, 208, 210. The information collector 308 collects the received information and the pain level determiner 322 automatically determines information indicative of a level of pain using the frequency spectrum.

It will be appreciated that information indicative of both, a visible and an audible feature of the patient may be used for determining the information indicative of a pain level experienced by the patient. One example may relate to capturing a video of the patient that includes images of facial features and a frequency spectrum from the voice of the patient.

In a further embodiment (not shown), there is provided a pain assessment system similar to pain assessment system 200 illustrated in FIGS. 2 and 3. However, in this particular example, instead of a network interface 304 and a web server 306, the pain assessment system comprises a capturing element. Specifically, the capturing element is arranged to capture information indicative of at least one visible and/or audible feature that is capable of indicating pain. A processor of the pain assessment system is arranged to determine information indicative of a level of pain experienced by the patient using the captured information. Similar to the pain assessment system 200, the pain assessment system in this example is arranged such that a patient-specific effect of a drug on pain experienced by the patient can be determined by comparing information indicative of a level of pain experienced by the patient after administration of the drug with reference information indicative of a reference level of pain. This pain assessment system may be implemented in the form of a user computing device such as a smart phone, a tablet or a laptop. However, other user computing devices are envisaged.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

What is claimed is:

1. A method for determining an effect of a drug on pain experienced by a patient, the method comprising:
   using a camera to capture positional information of at least one visible facial feature from the patient;
   comparing, using a processor of a pain assessment system, the positional information of the at least one visible facial feature to predetermined data for the at least one visible facial feature to determine reference information that is indicative of a reference level of the pain experienced by the patient;

after administering the drug to the patient using the camera to capture second information indicative of the at least one visible facial feature from the patient;

comparing, using the processor, the second information to the predetermined data for the at least one visible facial feature to determine pain indicating information associated with a level of pain experienced by the patient after administering the drug to the patient;

comparing, using the processor, the pain indicating information with the reference information to determine the effect of the drug on the pain experienced by the patient; and providing an alternative treatment to the patient for the pain experienced by the patient in response to determining that the effect of the drug is below a predetermined threshold.

2. The method of claim 1 wherein the step of comparing the second information to the predetermined data to determine the pain indicating information is conducted automatically using an algorithm.

3. The method of claim 1 wherein capturing positional information of the at least one visible facial feature comprises capturing further information indicative of the at least one visible facial feature of the patient before the drug is expected to have an effect on the pain experienced by the patient.

4. The method of claim 1 wherein the reference information is indicative of an expected level of pain after administration of the drug.

5. The method of claim 1 wherein the reference information is indicative of a level of the pain before administration of the drug.

6. The method of claim 1 further comprising:
receiving and storing information in relation to the drug and/or in relation to the patient, and
using the information in relation to the drug and/or information in relation to the patient to estimate a time period for the drug to have an expected effect on pain experienced by the patient,
wherein the step of using the camera to capture the second information indicative of the visible facial feature of the patient is conducted after the estimated time period has expired.

7. The method of claim 1 comprising a step of identifying a cause and/or determining treatment of the pain experienced by the patient based on the determined effect of the drug on pain.

8. The method of claim 1 wherein the step of using the camera to capture the positional information and/or the second information comprises using the camera to capture an image of the face of the patient.

9. A pain assessment system comprising:
an interface for receiving positional information concerning at least one visible facial feature that is indicative of a reference level of pain, and for receiving second information indicative of the at least one visible facial feature of a patient after administering a drug to the patient, the at least one visible facial feature being capable of indicating a pain level experienced by the patient, wherein the positional information and second information indicative of at least one visible facial feature of the patient are captured using a camera; and a processor arranged to:
compare the positional information to predetermined data for the at least one visible facial feature to determine reference information that is indicative of the reference level of the pain experienced by the patient,
compare the received second information to the predetermined data for the at least one visible facial feature to determine pain indicating information associated with a level of pain experienced by the patient,
compare the determined pain indicating information with the reference information such that an effect of the drug on the pain experienced by the patient can be determined, and
determine an alternative treatment to the patient based on the determined effect of the drug on the pain experienced by the patient being below a predetermined threshold.

10. The system of claim 9, wherein the processor is arranged to automatically determine the pain indicating information using an algorithm.

11. The system of claim 9 wherein the reference information is determined by the processor by using further information indicative of the at least one visible facial feature of the patient captured before the drug is expected to have an effect on the pain experienced by the patient.

12. The system of claim 9 wherein the reference information is indicative of an expected level of pain after administration of the drug.

13. The system of claim 9 wherein the interface is arranged to receive information in relation to the drug and/or information in relation to the patient, and wherein the processor is arranged to use the information in relation to the drug and/or the information in relation to the patient to estimate a time period for the drug to have an expected effect on pain experienced by the patient.

14. The system of claim 13 wherein the interface of the system is arranged to transmit information indicative of the estimated time period and/or the determined effect of the drug on pain via a communications network.

15. The system of claim 9, wherein the received positional information and/or second information indicative of the at least one visible facial feature comprises an image of the face of the patient.

16. The system of claim 9, wherein the at least one visible facial feature of the patient relates to one or more of the following:
behavioural change,
psychological change,
physiological change, and physical change.

* * * * *